(12) United States Patent
Wang et al.

(10) Patent No.: US 10,365,234 B2
(45) Date of Patent: Jul. 30, 2019

(54) APPARATUS AND METHOD FOR INSPECTING MOVING TARGET

(71) Applicants: Tsinghua University, Beijing (CN); Nuctech Company Limited, Beijing (CN); BEIJING HUALIXING SCI-TECH DEVELOPMENT CO., LTD., Beijing (CN)

(72) Inventors: Liming Wang, Beijing (CN); Haibo Qu, Beijing (CN); Xilong Liu, Beijing (CN); Jie Zhao, Beijing (CN)

(73) Assignees: Tsinghua University, Beijing (CN); Nuctech Company Limited, Beijing (CN); Beijing Hualixing Sci-Tech Development Co., Ltd., Beijing (CN)

( * ) Notice: Subject to any disclaimer, the term of this patent is extended or adjusted under 35 U.S.C. 154(b) by 171 days.

(21) Appl. No.: 15/503,676

(22) PCT Filed: Aug. 19, 2015

(86) PCT No.: PCT/CN2015/087550
§ 371 (c)(1),
(2) Date: Feb. 13, 2017

(87) PCT Pub. No.: WO2016/026442
PCT Pub. Date: Feb. 25, 2016

(65) Prior Publication Data
US 2017/0269006 A1    Sep. 21, 2017

(30) Foreign Application Priority Data

Aug. 19, 2014 (CN) .......................... 2014 1 0409522
Aug. 19, 2014 (CN) .......................... 2014 1 0410432

(51) Int. Cl.
*G01N 23/00* (2006.01)
*G01N 23/04* (2018.01)
(Continued)

(52) U.S. Cl.
CPC .............. *G01N 23/04* (2013.01); *G01B 7/003* (2013.01); *G01V 5/0016* (2013.01);
(Continued)

(58) Field of Classification Search
CPC ........................ G01N 2223/201; G01V 5/0008
See application file for complete search history.

(56) References Cited

U.S. PATENT DOCUMENTS

| 2008/0037707 A1 | 2/2008 | Rothschild et al. |
| 2009/0225939 A1* | 9/2009 | Chen .................... G01V 5/0016 378/62 |

(Continued)

FOREIGN PATENT DOCUMENTS

| CN | 2752763 | 1/2006 |
| CN | 101162205 | 4/2008 |

(Continued)

OTHER PUBLICATIONS

European Extended Search Report dated Mar. 12, 2018 for corresponding European Application No. 15834549.6 in 19 pages.

(Continued)

*Primary Examiner* — Dani Fox
(74) *Attorney, Agent, or Firm* — Knobbe, Martens, Olson & Bear LLP

(57) ABSTRACT

An apparatus and method for quick imaging and inspection of a moving target. The apparatus comprises a passage, a scanning and imaging device (106), a first position sensor (101), a second position sensor (103), and a control unit (105). The control unit (105) powers on an electron induction accelerator in the scanning and imaging device (106) to make the electron induction accelerator enter a standby state when the control unit (105) receives from the first position sensor (101) a detection signal indicating that a moving target (100) enters the passage, and controls a beam emitting (Continued)

time point and a beam emitting mode of the electron induction accelerator to correspondingly inspect different parts of the moving target (100) when the second position sensor (103) detects that different sections pass through a radiation scanning area. The driver and passengers do not need to get off when a traveling vehicle is inspected, the apparatus controls the accelerator to emit ray beams with corresponding energy to perform scanning when the moving target passes through the scanning area, flexible scanning is realized, and inspection time is reduced.

17 Claims, 4 Drawing Sheets

(51) Int. Cl.
    *G01B 7/00*     (2006.01)
    *G01V 5/00*     (2006.01)

(52) U.S. Cl.
    CPC .................. *G01N 2223/201* (2013.01); *G01N 2223/3307* (2013.01); *G01N 2223/631* (2013.01)

(56) References Cited

U.S. PATENT DOCUMENTS

| | | |
|---|---|---|
| 2009/0316136 A1 | 12/2009 | Chen et al. |
| 2011/0268247 A1 | 11/2011 | Shedlock et al. |
| 2011/0274242 A1 | 11/2011 | Linev |
| 2012/0195403 A1 | 8/2012 | Vedantham et al. |
| 2017/0090062 A1 | 3/2017 | Cao et al. |

FOREIGN PATENT DOCUMENTS

| | | |
|---|---|---|
| CN | 101162209 | 4/2008 |
| CN | 101162507 | 4/2008 |
| CN | 101501477 | 8/2009 |
| CN | 102147486 | 8/2011 |
| CN | 102834738 | 12/2012 |
| CN | 103984035 | 8/2014 |
| CN | 204241395 | 4/2015 |
| EP | 1970700 A1 | 9/2008 |
| WO | WO 2008/054410 | 5/2008 |
| WO | WO 2013/119423 | 8/2013 |

OTHER PUBLICATIONS

First Office Action and Search Report dated Apr. 10, 2017 in Chinese Application No. 201410410432.X (6 pgs), and concise English-language summary of same (1 pg); 7 pgs total.

First Office Action and Search Report dated Apr. 21, 2017 in Chinese Application No. 201410409522.7 (10 pgs) and concise English-language summary of same (1 pg); 11 pgs total.

International Search Report (4 pgs) and Written Opinion (4 pgs) received in parent International Application No. PCT/CN2015/087550, dated Oct. 30, 2015, as well as English-language translation of ISR (3 pgs); 11 pages total.

\* cited by examiner

APPARATUS AND METHOD FOR INSPECTING MOVING TARGET

CROSS-REFERENCE TO RELATED APPLICATIONS

This application is a U.S. 371 National Phase of International application No. PCT/CN2015/087550, filed Aug. 19, 2015, published as WO2016/026442A1, which is based upon and claims priority to Chinese Patent Application No. 201410410432.X and Chinese Patent Application No. 201410409522.7 both filed on Aug. 19, 2014, all of which are incorporated herein by reference in entirety.

TECHNICAL FIELD

The present disclosure relates to a process of scanning and imaging a moving target, and in particular to an apparatus and method for imaging and inspecting a moving target.

BACKGROUND

An apparatus for inspecting a vehicle by using high-energy rays is a typical example of equipment for imaging and inspecting a moving target. In the apparatus for inspecting the vehicle by using the high-energy rays, a dragging device is typically used to drag the inspected vehicle to move at a constant speed, while an accelerator continuously emits high-frequency rays at a fixed frequency. Such an apparatus has a baffle plate which is capable of shielding the rays and used to control whether the high-energy rays are emitted to the inspected vehicle. When the baffle plate is opened, the high-energy rays are emitted to the inspected target to scan and image the vehicle, thereby performing the inspection.

In such a conventional apparatus, the accelerator is normally placed in an open state, resulting in the following disadvantages: a power consumption of the apparatus is high; a temperature of the apparatus is always very high, and thus a large cooling device is necessary, which will occupy a large space; a service life of the accelerator may be affected as it is powered on for a long time, and thus product cost is relatively high; and dark electrons may be generated as the accelerator is always on, resulting in a potential risk. Furthermore, since the emission of the high-energy rays is controlled by the opening and closing of the mechanical baffle plate, a response speed is slow, leading to a long inspection time and a low inspection rate for the vehicle.

SUMMARY

In consideration of the problems in the prior art, an object of the present disclosure is to provide an apparatus and method for imaging and inspecting a moving target.

According to one aspect of the present disclosure, a fast imaging and inspection apparatus for a moving target is provided, and comprises a passage for the moving target to pass therethrough; a scanning and imaging device, comprising a betatron for generating X-rays, and a detector for receiving X-rays penetrating through the moving target, wherein the betatron images the moving target by emitting the X-rays to the moving target passing through the passage; a first position sensor, disposed at a position away from and on one side of the scanning and imaging device and configured to output a sensing signal indicating whether the moving target begins to enter the passage; a second position sensor, disposed between the first position sensor and the scanning and imaging device, and configured to detect a type feature of the moving target, distinguish a protected part of the moving target from an unprotected part of the same, section the moving target, and output a sensing signal indicating whether the protected part of the moving target is passing or has already passed through a radiation scanning area; and a control unit, connected to the scanning and imaging device, the first position sensor and the second position sensor, and configured to power on the betatron to place it in a standby state upon receiving the sensing signal indicating that the moving target begins to enter the passage from the first position sensor, and control a beam emitting time-point and a beam emitting mode of the betatron to correspondingly inspect respective sections of the moving target when the second position sensor detects that the respective sections are passing through the radiation scanning area.

According to some implementations, a distance between the first position sensor and the scanning and imaging device is set to be greater than a predetermined value, such that a time period from a moment when the first position sensor detects the moving target to a moment when the moving target begins to enter the radiation scanning area is longer than or equal to a time period by which the betatron is powered on to reach the standby state.

According to some implementations, the apparatus further comprises a speed sensor, which is disposed between the first position sensor and the scanning and imaging device, and configured to measure a moving speed of the moving target in the passage, wherein upon receiving the sensing signal indicating that the moving target begins to enter the passage from the first position sensor, the control unit controls the speed sensor to measure the moving speed of the moving target, controls reconstruction of a scanned image based on the moving speed of the moving target received from the speed sensor, and corrects data of the scanned image based on the moving speed.

According to some implementations, the moving target passes through the passage at a speed in a predetermined speed range: if the moving target has a speed at an upper limit of the predetermined speed range, the scanning and imaging device performs sampling at a beam emitting frequency of the betatron; and if the moving target has a speed below the upper limit of the predetermined speed range, the scanning and imaging device is in an oversampling state, and the reconstruction of the scanned image is performed with an interpolation method or a convolution method.

According to some implementations, an overall vehicle scanning or a sectional scanning is performed on a car, a coach, a container truck, and a van, allowing passing thereof without requiring drivers to get off.

According to some implementations, the second position sensor is further configured to detect and recognize non-vehicles, cars, coaches, container trucks of trailer type, and vans.

According to some implementations, instruction according to a sensing signal from the second position sensor, to switch an operating timing of a deflection coil of the betatron and thereby generate X-rays with different energy.

According to some implementations, the apparatus further comprises a third position sensor which is configured to determine whether the moving target has moved out of the passage, wherein the control unit sends a control signal to stop power supply to the betatron after the third position sensor detects that the moving target has entirely moved out of the radiation scanning area.

According to some implementations, the first position sensor comprises a first ground induction coil buried underground at an entry to the passage, and first rapid-response light curtain switches disposed at two sides of the passage for use in conjunction with the first ground induction coil.

According to some implementations, pillars are installed at the two sides of the passage, and the rapid-response light curtain switches are disposed on the respective pillars.

According to some implementations, the speed sensor comprises speed radar detectors disposed at the two sides of the passage.

According to some implementations, the second position sensor comprises second rapid-response light curtain switches disposed at the two sides of the passage, and photoelectric switches also disposed at the two sides of the passage.

According to some implementations, the third position sensor comprises a second ground induction coil buried underground and near an exit in the passage, and third rapid-response light curtain switches disposed at the two sides of the passage.

According to another aspect of the present disclosure, a method for fast imaging and inspecting a moving target is provided, which comprises steps of outputting from a first position sensor a sensing signal indicating whether a moving target begins to enter a passage for the moving target to pass therethrough; detecting a type feature of the moving target, distinguishing a protected part of the moving target from an unprotected part of the same, sectioning the moving target, and outputting a sensing signal indicating whether the protected part of the moving target is passing or has already passed through a radiation scanning area, by use of a second position sensor; powering on a betatron of a scanning and imaging device to place it in a standby state, upon receiving the sensing signal indicating that the moving target begins to enter the passage from the first position sensor, wherein the scanning and imaging device comprises the betatron for generating X-rays, and a detector for receiving X-rays penetrating through the moving target, and the betatron emits X-rays to the moving target passing through the passage to image the moving target; and controlling a beam emitting time-point and a beam emitting mode of the betatron to correspondingly inspect respective sections of the moving target, when the second position sensor detects that the respective sections are passing through the radiation scanning area.

According to some implementations, a distance between the first position sensor and the scanning and imaging device is set to be greater than a predetermined value, such that a time period from a moment when the first position sensor detects the moving target to a moment when the moving target begins to enter the radiation scanning area is longer than or equal to a time period by which the betatron is powered on to reach the standby state.

According to some implementations, the method further comprises a step of: measuring a moving speed of the moving target in the passage by use of a speed sensor disposed between the first position sensor and the scanning and imaging device; and controlling the speed sensor to measure the moving speed of the moving target upon receiving the sensing signal indicating that the moving target begins to enter the passage from the first position sensor, and controlling reconstruction of the scanned image based on the moving speed of the moving target received from the speed sensor, and correcting data of the scanned image based on the moving speed.

According to some implementations, the moving target passes through the passage at a speed in a predetermined speed range: if the moving target has a speed at an upper limit of the predetermined speed range, the scanning and imaging device performs sampling at a beam emitting frequency of the betatron; and if the moving target has a speed below the upper limit of the predetermined speed range, the scanning and imaging device is in an oversampling state, and the reconstruction of the scanned image is carried out with an interpolation method or a convolution method.

According to some implementations, the method further comprises a step of: determining whether the moving target has moved out of the passage by use of a third position sensor, and sending a control signal to stop power supply to the betatron after the third position sensor detects that the moving target has entirely moved out of the radiation scanning area.

According to some implementations, the moving target is, for example, a moving vehicle, and the part to be protected is the head part of the vehicle.

In the implementation of the present disclosure, an apparatus for inspecting a vehicle by using high-energy rays is provided for inspection while the vehicle is traveling without requiring the driver and passengers to get off. The apparatus controls a betatron to emit ray beams with corresponding energy for scanning at an extremely high response speed when the moving target passes through a scanning area (as required by users, an overall scanning may be performed on the inspected moving target, or the protected part may not be scanned). A flexible scanning is realized, and an inspection time can be shortened.

Through the above technical solutions in the present disclosure, the vehicle passing rate can be increased to more than 200 container trucks per hour. Compared with the prior art, the technical solution of the present disclosure can greatly increase a vehicle inspection rate, and significantly reduce an energy consumption and equipment costs. Additionally, since there is no need to use the large cooling device, a floor area of the entire apparatus is small, such that the apparatus is applicable to various road block ports.

BRIEF DESCRIPTION OF THE DRAWINGS

To provide better understanding of the present disclosure, the implementations of the present disclosure will be described according to the following accompanying drawings.

Not all circuits or structures of the implementations are shown in the figures. Like reference numbers throughout all the figures refer to like or similar components or features.

DETAILED DESCRIPTION

The specific implementations of the present disclosure will be described in detail below. It should be noted that the implementations described herein are merely used for illustrating by way of examples, rather than limiting, the present disclosure. In the following descriptions, numerous specific details are set forth in order to provide thorough understanding of the present disclosure. However, it is apparent for those skilled in the art that such specific details are not necessarily required to implement the present disclosure. In other examples, to avoid confounding with the present disclosure, the well-known circuits, materials or methods are not described in details.

In the entire description, the presentation of "one implementation", "implementations", "one example", or "examples" means that specific features, configurations or characteristics described in conjunction with this implementation(s) or example(s) are contained in at least one implementation of the present disclosure. Hence, the phrases "in one implementation", "in the implementations", "in an example", or "examples" used in various parts of the entire description do not certainly refer to the same implementation or example. In addition, specific features, configurations or characteristics may be combined in one or more implementations or examples in any appropriate combinations and/or sub-combinations. Moreover, it will be understood by those skilled in the art that the accompanying figures provided herein are intended for illustration, and not certainly drawn to scale. It should be appreciated that, for the description that a member is "coupled" or "connected" to another member, the member may be directly coupled or connected to another member, or an intermediate member may be present. On the contrary, for the description that a member is "directly coupled" or "directly connected" to another member, no intermediate member is present. Similar reference numbers denote similar members. As used herein, the term "and/or" includes any and all the combinations of one or more relevant listed items.

The apparatus for imaging and inspecting a moving target of the present disclosure will be described below with reference to the accompanying figures. As shown in the figures, fast inspection apparatus for a vehicle is described as an implementation. The following descriptions are intended for explaining the present disclosure in conjunction with an example without limiting the present disclosure thereto.

Figure 1:
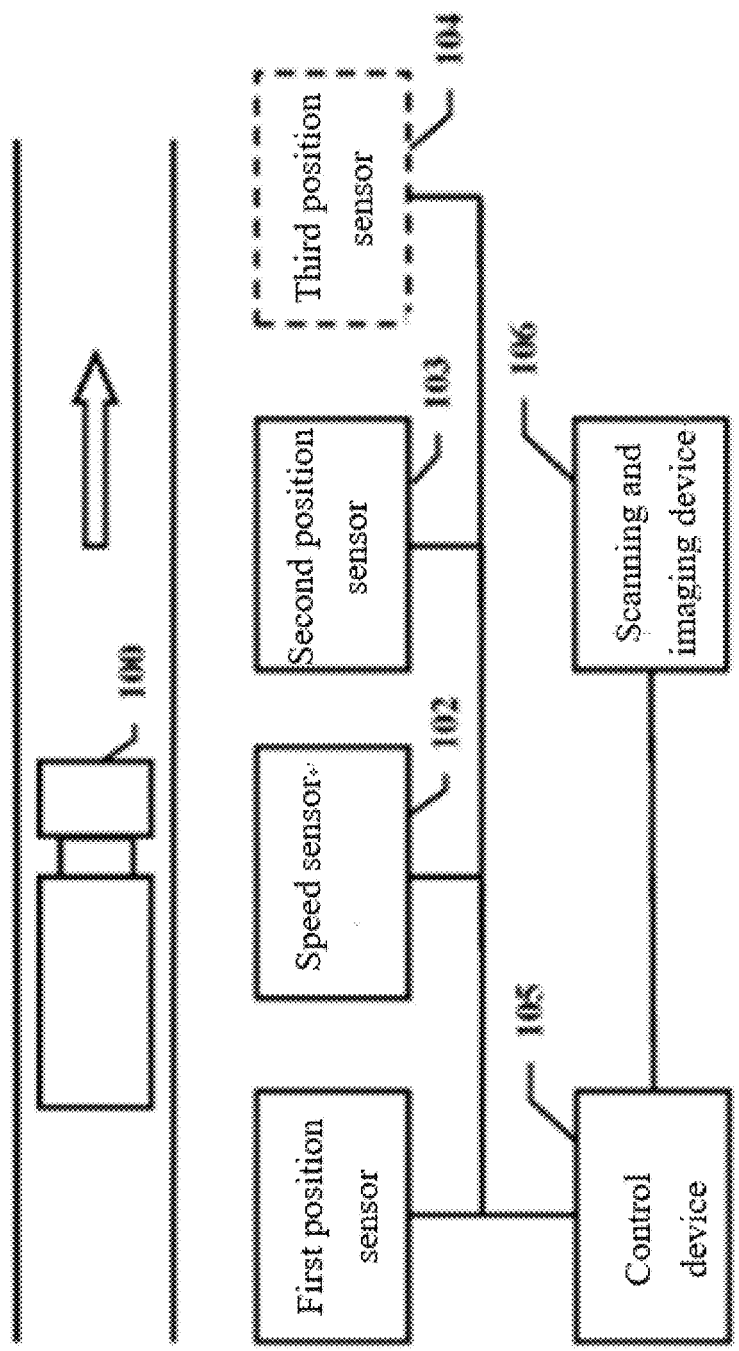
FIG. 1 is a structural schematic diagram of an inspecting apparatus according to an implementation of the present disclosure.

FIG. 1 shows a fast imaging and inspection apparatus for a vehicle according to an implementation of the present disclosure, wherein ray beams with different energy are emitted to different sections of a moving target to achieve fast imaging and inspection. As shown in FIG. 1, in the implementation of the present disclosure, a moving target 100, such as a vehicle, enters an inspection passage, and then is detected by a first position sensor 101. A control device 105 sends an instruction to activate a betatron in a scanning and imaging device 106, and the betatron is powered on to be placed in a standby state.

A second position sensor 103 detects a type feature of the moving target, distinguishes a protected part of the moving target from an unprotected part of the same, correctly sections the moving target (e.g., a driving cab section and unprotected remaining part), and outputs respective sensing signals indicating that the protected part of the moving target is passing and has already passed through a scanning area.

The control device 105 powers on the betatron to place the betatron in the standby state upon receiving a sensing signal indicating that the moving target begins to enter the passage from the first position sensor 101, and controls a beam emitting time-point and a beam emitting mode of the betatron to correspondingly inspect the two parts of the moving target, when the second position sensor detects that the respective parts of the moving target are passing through the radiation scanning area. For example, rays with low energy are used to inspect the driving cab, such that dose of rays received by the driving cab is extremely low; therefore, the driver can stay in the vehicle. However, for such a part as a container, rays with high energy are used for inspection to obtain a clear image of a target part.

The scanning and imaging device 106 comprises the betatron for generating X-rays, and a detector for receiving X-rays penetrating through the moving target. The betatron emits X-rays to the moving target passing through the passage to image the moving target. The first position sensor 101 is disposed at a position away from and on one side of the scanning and imaging device, and configured to output the sensing signal indicating whether the moving target begins to enter the passage. The second position sensor 103 is disposed between the first position sensor 101 and the scanning and imaging device 106, and configured to detect the type feature of the moving target, distinguish the protected part from the unprotected part of the moving target, correctly section the moving target, and output respective sensing signals indicating that the protected part of the moving target is passing and has already passed through the scanning area.

The control device 105 is connected to the scanning and imaging device 106, the first position sensor 101, and the second position sensor 103, and configured to power on the betatron to place the betatron in the standby state upon receiving the sensing signal indicating that the moving target begins to enter the passage from the first position sensor 101, and control the beam emitting time-point and the beam emitting mode of the betatron to correspondingly inspect the two parts of the moving target when the second position sensor 103 detects that the respective parts of the moving target are passing through the radiation scanning area.

In the illustrated implementation, a distance between the first position sensor 101 and the scanning and imaging device 106 is set to be greater than a predetermined value, such that a time period from a moment when the first position sensor detects the moving target to a moment when the moving target begins to enter the radiation scanning area is longer than or equal to a time period by which the betatron is powered on to be placed in the standby state.

As shown in FIG. 1, the inspecting apparatus may further comprise a speed sensor 102 which is disposed between the first position sensor 101 and the scanning and imaging device 106, and configured to measure a moving speed of the moving target in the passage. The control unit 105 controls the speed sensor 102 to measure the moving speed of the moving target upon receiving the sensing signal indicating that the moving target begins to enter the passage from the first position sensor 101, controls reconstruction of the scanned image based on the moving speed of the moving target received from the speed sensor 102, and corrects data of the scanned image based on the moving speed.

For example, the moving target passes through the passage at a speed in a predetermined speed range. If the moving target has a speed at an upper limit of the predetermined speed range, the scanning and imaging device 106 performs sampling at a beam emitting frequency of the betatron. If the moving target has a speed below the upper limit of the predetermined speed range, the scanning and imaging device 106 is in an oversampling state, and the reconstruction of the scanned image may be performed with an interpolation method or a convolution method.

As shown in FIG. 1, the inspection apparatus may further comprise a third position sensor 104. The third position sensor 104 is configured to determine whether the moving target has entirely moved out of the passage; and the control device 105 may send a control signal to stop power supply to the betatron, after the third position sensor 104 detects that the moving target has entirely moved out of the radiation scanning area. In other implementations, if there is still other vehicles following the inspected vehicle, as detected by the first position sensor 101, the control device 105 sends no control signal to stop power supply to the betatron.

Figure 2:
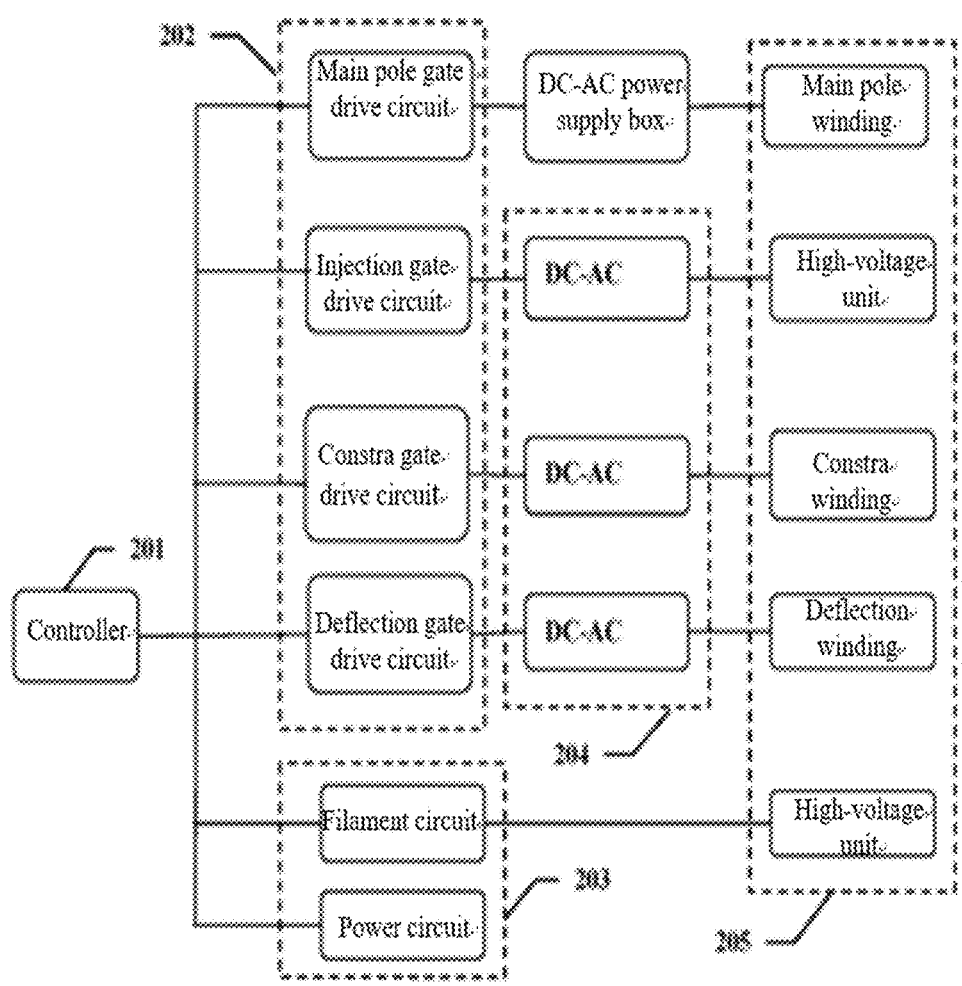
FIG. 2 shows a structural schematic diagram of a betatron used in the inspecting apparatus of FIG. 1.

FIG. 2 shows a structural schematic diagram of the betatron used in the inspection apparatus as shown in FIG. 1. The betatron is a cyclotron in which electrons move along a circular trajectory in a vacuum acceleration chamber, and simultaneously, obtains sufficient energy through a vortex electric field. The vortex electric field is caused by changes of magnetic flux pulses, and can control the motion trajectories of the electrons while providing energy to them.

In the system as shown in FIG. 2, the betatron mainly comprises: a radiator 205, a power supply unit 203, a pulse converter 204, and an interface unit (not shown). The radiator includes a high-voltage injection unit assembly, an acceleration chamber, a main pole and a pole winding, a deflection winding, a Constra winding (a constraint winding), an ionization chamber, etc. In an implementation, the interface unit, for example, converts RS-422 digital signals and corresponding protocols into USB standard signals usable for a computer.

The pulse converter 204 is configured to generate a current pulse of a Constra (a constraint) and that of a deflection system, and a voltage pulse of an injection system. The converter may provide three kinds of output voltages: (1) a 400V voltage for an injection voltage generator (the injection voltage generator is activated by a synchronization plate of the power supply unit (a thyristor is activated), and a double-chain line will discharge to a primary winding of a high-voltage transformer of the injection unit, thereby generating a high-voltage pulse on a secondary winding of the transformer); (2) a 360V voltage for a constraint current generator; the synchronization plate will trigger the constraint current generator (the thyristor is activated); and (3) a 560V voltage for a deflection current generator. The deflection current generator may be triggered when an actuator receives a pulse from the synchronization plate (an IGBT transistor is activated). A coupling member for connecting other units, a main power switch and an operation control function in the power supply unit are all located on a same panel. A power converter is powered by a three-phase 220/380V power source. The power converter is used for exciting a magnet of the betatron. The power converter includes a three-phase rectifier, a two-stage transistor bridge based on an IGBT three-stage transistor (a switchboard), an energy input thyratron, and a protector.

As shown in FIG. 2, the betatron also comprises a power supply device 203 providing a voltage and a filament voltage, a synchronizing device 202, and a controller 201. The power supply device 203 provides a +12V voltage to a filament control circuit before activation of the magnet, and the voltage will reduce an output voltage of a filament, such that the filament is placed in a standby mode. When radiation is activated, the voltage provided to the filament control circuit turns to 0, and the output voltage of the filament will be increased by 2-3V. When radiation is turned off, the output voltage of the filament is reduced, such that the service life of the acceleration chamber may be prolonged. The synchronizing device 202 may, in a specific time sequence, send a control signal to the betatron, transmit a timing signal Beam Trig (triggering electron beams) to a goods detection system (CIS), controls a radiation switch through external signals RAD ON (activating radiation) from the goods detection system and process emergency stop signals. The controller 201 is provided with a peripheral device for controlling the operation of the betatron, and configured to control the power converter, stabilize the voltage of an electromagnet, and regulate the energy of electrons.

Figure 3:
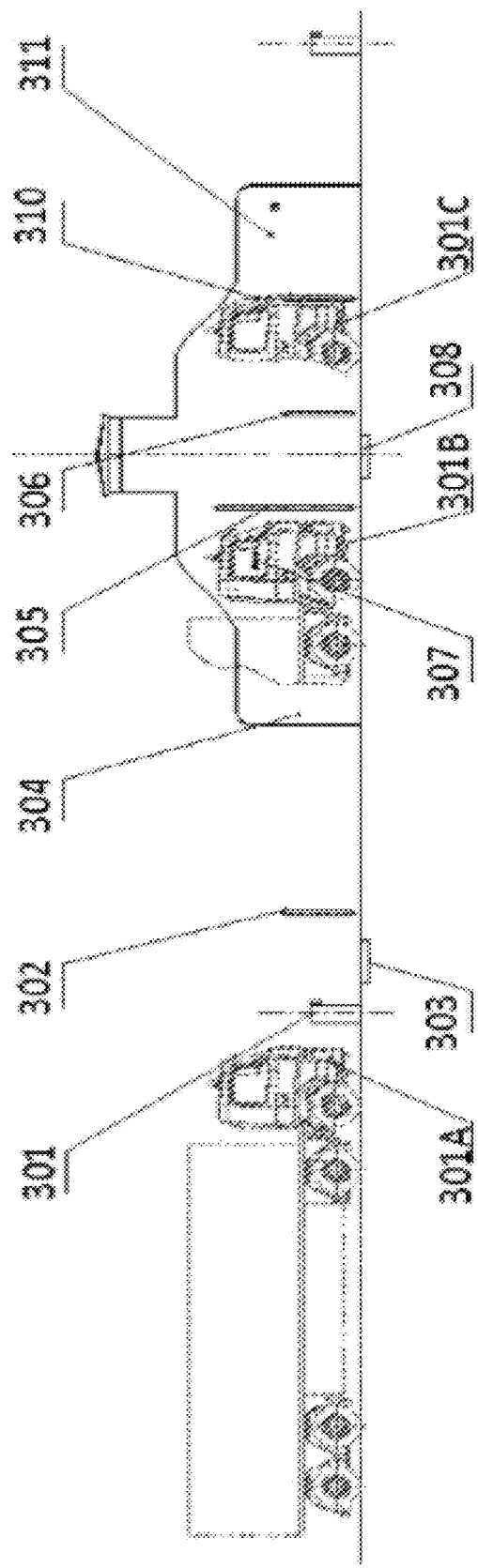
FIG. 3 and FIG. 4 are schematic diagrams describing the inspecting methods according to implementations of the present disclosure.
Figure 4:
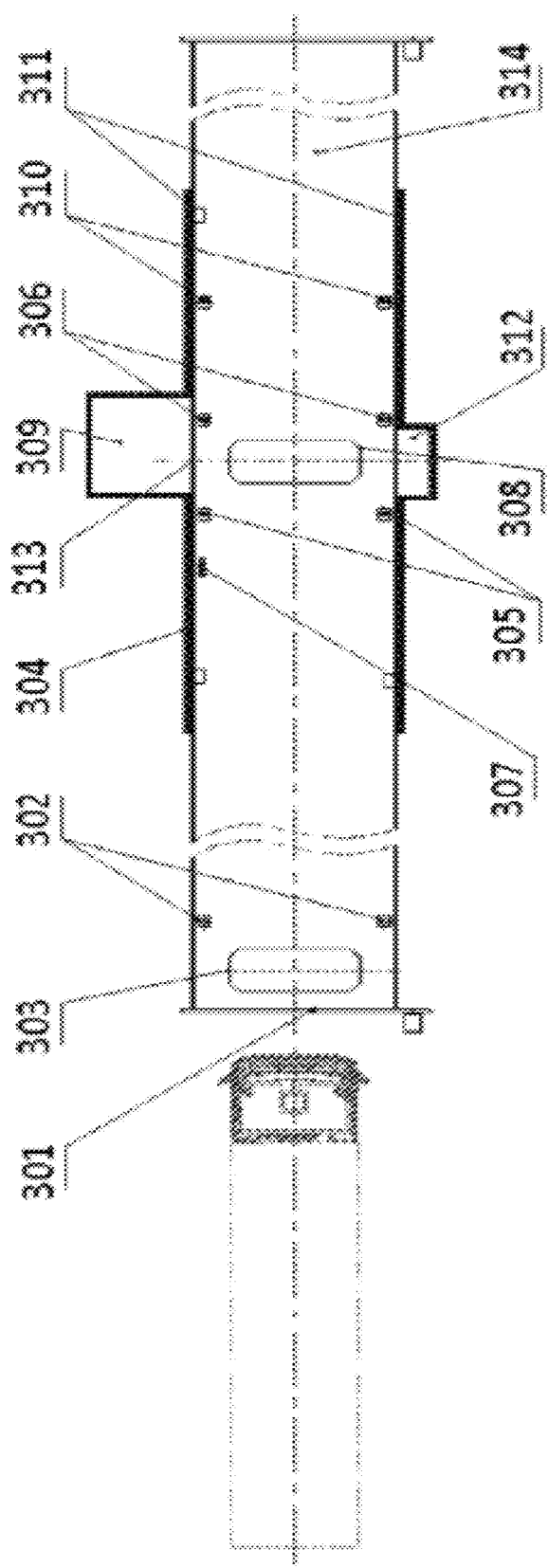

FIG. 3 and FIG. 4 are schematic diagrams describing an inspecting method according to an implementation of the present disclosure, wherein FIG. 4 is a schematic top view of the apparatus of FIG. 3. As shown in FIG. 3 and FIG. 4, a fast imaging and inspection apparatus comprises a betatron cabin 309, rapid-response light curtain switches 302, 305 and 306, ground induction coils 303 and 308, photoelectric switches 310, protection walls 304 and 311, a speed radar detector 307, a detector arm 312, control software, etc. The rapid-response light curtain switches 302 are installed on installation pillars disposed at two sides of a passage. The ground induction coil 303 is buried underground at an entry to the passage, serving as a first switch for the entry of the vehicle. The protection walls 304, 311 are vertically erected at two sides of the passage, and respectively connected to the betatron cabin 309 and the detector arm 312 that are respectively disposed at the two sides of the passage. The rapid-response light curtain switches 305, 306 are installed on a wall of the betatron cabin 309 and the detector arm 312, wherein the betatron cabin 309 and the detector arm 312 are respectively disposed at the two sides of the passage. The photoelectric switches 310 are installed on the protection walls 311 disposed at the two sides of the passage. The speed radar detector 307 is installed on an external wall, close to the passage, of the betatron cabin 309. The ground induction coil 308 is buried underground near an exit in the passage. The operating process of the present disclosure will be described below.

When the number of vehicles in the passage is zero, the system is in the standby state. When a vehicle 301A moves toward the passage, the ground induction coil 303 works first, and a determination is made on a traveling direction of the vehicle in conjunction with the rapid-response light curtain switches 302. If the vehicle moves into the passage, 1 is added to the number of vehicles in the passage; the speed radar detector 307 measures the moving speed of the vehicle, and the system becomes a ready state. The vehicle continues to move forward, and the system records all the state changes of the vehicle during the movement thereof in the passage.

When the vehicle arrives 301C from 301A through 301B at a normal speed, the photoelectric switches 310 work. At this time, it is determined whether the vehicle is a container truck or a van according to the states of the light curtain switches 305. Different scanning triggering conditions are adopted according to different vehicle types.

After the rapid-response light curtain switches 302 detect that the vehicle begins to enter an inspection area, if the vehicle is determined as the container truck based on the states of the light curtain switches 305, it is detected whether the driving cab of the vehicle has passed and then a passing signal is generated, the scanning inspection can be carried out when the container arrives at the inspection area. The control system generates a control signal for controlling the betatron system to generate electron beams based on the passing signal sent by detectors.

The third position sensor 104, for example, comprises the rapid-response light curtain switches 306 and the ground induction coil 308 as shown in FIG. 3 and FIG. 4. The ground induction coil 308 is buried underground at a position near the exit in the passage, and is used in conjunction with the rapid-response light curtain switches 306 disposed at the two sides of the passage to detect whether a vehicle has moved out of the scanning passage. When the vehicle has moved out of the scanning passage, 1 is subtracted from the number of vehicles in the passage. The system remains in the ready state as long as the number of vehicles in the passage is not zero. When the number of vehicles in the passage is zero, the system is placed into the standby state.

In an implementation of the present disclosure, when the sensors, for example, the ground induction coil 303 and the light curtain switches 302, disposed at a front end of the passage, detects that a vehicle begins to enter the passage, the control device 105 controls the betatron in the scanning and an imaging device to be powered on such that an electron gun of the betatron generates an electron beam. The generated electron beam is injected into a gyration track constituted by the magnet winding to be accelerated. After being accelerated to a predetermined electron energy, for example, accelerated to several M electron volts, the accelerated electron beam is extracted through the deflection winding to bombard a target and generate X-rays. During acceleration, the Constra winding gathers the electron beam to prevent diverging thereof.

In the above implementations, the above switches 302 may be formed as the first rapid-response light curtain switches, the above switches 305 may be formed as the second rapid-response light curtain switches, the above switches 306 may be formed as the third rapid-response light curtain switches, and the above switches 310 may be formed as the photoelectric switches. In other implementations, the photoelectric switches can also be used together with another rapid-response light curtain switch.

The second position sensor 103 may comprise the second rapid-response light curtain switches 305. For example, after the second rapid-response light curtain switches 305 are employed to detect the type of vehicle, the time of emitting a beam for scanning is determined based on the detection result. That is, avoidance of being scanned for the vehicle head (driving cab) also can be realized, by delaying the beam emitting time for a period of time based on the vehicle speed detected by the speed sensor 102 and the information on the type of vehicle detected by the second position sensor 103.

The second position sensor 103 may also comprise the second rapid-response light curtain switches 305 and the photoelectric switches 310, for example, in other implementations. For example, in order to more accurately determine the beginning time of the beam to be emitted as the vehicle compartment is passing through the scanning area after the vehicle head has passed through the scanning area for avoidance of being scanned, the photoelectric switches 310 can be disposed at a position having a certain distance (e.g., preferably, a value of the length of the longest vehicle head among various types of vehicle) away from the scanning area. When the photoelectric switches 310 detects the vehicle head, which means that the vehicle head, of which the scanning needs to be avoided, has already passed through the scanning area and the vehicle compartment is going to pass through the scanning area, the beam is emitted for scanning. In this way, the photoelectric switches 310 may also be used in conjunction with the second rapid-response light curtain switches 305.

In some implementations, the second position sensor 103 detects the type feature of the moving target, distinguishes the protected part of the moving target from the unprotected part thereof, sections the moving target, and outputs the sensing signal indicating whether the protected part of the moving target is passing or has already passed through the radiation scanning area. For example, the type of the moving target may be determined as a container truck, a van, or the like, and the scanning mode of a predetermined type is employed based on the type of vehicle. For example, if the moving target is determined as a coach, the coach does not need to be scanned. If the moving target is determined as a van, a beam is emitted for scanning. If the moving target is determined as a container truck, a certain time period is delayed, and a beam is emitted for scanning when the head part has moved out of the radiation scanning area and the container arrives at the radiation scanning area. Alternatively, an X-ray beam with a first energy is used for the head part of the container truck, while an X-ray beam with a second energy is used for the container part, with the first energy being about one third or even less of the second energy.

As such, after dividing the vehicle into multiple sections, the control unit controls a beam emitting time-point and a beam emitting mode of the betatron to correspondingly inspect respective sections of the moving target upon the second position sensor detects that the respective sections are passing through the radiation scanning area, and corrects the data of the scanned image based on the vehicle speed.

For example, in some implementations, an overall vehicle scanning or a sectional scanning is performed on a car, a coach, a container truck, and a van, allowing passing thereof without requiring drivers to get off. As another example, the second position sensor is also configured to detect and recognize non-vehicles, cars, coaches, container trucks of trailer type, and vans.

Due to extremely short time for the betatron to switch among different operating timings, the control unit may send an instruction based on the sensing signals from the second position sensor, to switch the operating timings of the deflection coil of the betatron to generate X-rays with different energy. For example, by setting different operating timings, the X-ray beam with the first energy may be used for the protected part, for example, the driving cab, while the X-ray beam with the second energy may be used for the unprotected part, with the first energy being about one third or even less of the second energy. Thus, different sections of a moving vehicle may be scanned in different scanning modes. For example, in the case that the first energy is 2.5 MeV and the second energy is 7.5 MeV, the exposure dose received by the driving cab is about 30% of that received by the container; therefore, in this case, the inspection can be performed without requiring the driver to get off.

In other implementations, the control unit performs safety inspection in different operating modes according to sensing signals of sensors. For example, during continuous operation where vehicles line up in succession for safety inspection, the betatron may be switched between the standby state and the operating state. As another example, in an intermittent operating mode, when few vehicles sparsely pass by for safety inspection, the betatron may be switched between a powered-on state and a powered-off state.

According to the solutions of some implementations, inspection is performed during the moving of the vehicle and without requiring the driver and passengers to get off. The apparatus can control the betatron to emit ray beams of different energy at an extremely high response speed and scan the moving target, when it passes through the scanning area (as required by users, an overall scanning may be performed to the inspected moving target, or no scanning may be performed to the protected part). Flexible scanning is realized, and an inspection time can be shortened.

Thus, since the inspected vehicle quickly passes through the inspection passage and the safety of the driver should be guaranteed when the vehicle is subjected to inspection, the system sends corresponding beam emitting instructions (enabling signals for enabling the electron gun) to the betatron for respective sections. Through the use of the present betatron system, a vehicle inspection efficiency can be greatly improved, and an equipment cost of the system can be reduced. With the above apparatus, a safe and reliable imaging inspection can be carried out on a fast moving target.

While the present disclosure is described with reference to several typical implementations, it will be understood that the used terms are illustrative, exemplary, and non-limiting. Since the present disclosure can be specifically implemented in various forms without departing from the spirit or essence of the disclosure, it will be understood that the above implementations are not limited to any foregoing details and should be extensively interpreted within the spirit and the scope defined by the appended claims. Therefore, all variations and modifications falling within the claims or the equivalent scope thereof should be covered by the appended claims.

What is claimed is:

1. A fast imaging and inspection apparatus for a moving target, comprising:
    a passage for the moving target to pass therethrough;
    a scanning and imaging device, comprising a betatron for generating X-rays, and a detector for receiving X-rays penetrating through the moving target, wherein the betatron images the moving target by emitting the X-rays to the moving target passing through the passage;
    a first position sensor, disposed at a position away from and on one side of the scanning and imaging device and configured to output a sensing signal indicating whether the moving target begins to enter the passage;
    a second position sensor, disposed between the first position sensor and the scanning and imaging device, and configured to detect a type feature of the moving target, distinguish a protected part of the moving target from an unprotected part of the same, section the moving target, and output a sensing signal indicating whether the protected part of the moving target is passing or has already passed through a radiation scanning area; and
    a control unit, connected to the scanning and imaging device, the first position sensor and the second position sensor, and configured to power on the betatron to place it in a standby state upon receiving the sensing signal indicating that the moving target begins to enter the passage from the first position sensor, and control a beam emitting time-point and a beam emitting mode of the betatron to correspondingly inspect respective sections of the moving target when the second position sensor detects that the respective sections are passing through the radiation scanning area,
    wherein a distance between the first position sensor and the scanning and imaging device is set to be greater than a predetermined value, such that a time period from a moment when the first position sensor detects the moving target to a moment when the moving target begins to enter the radiation scanning area is longer than or equal to a time period by which the betatron is powered on to reach the standby state.

2. The apparatus according to claim 1, further comprising a speed sensor, which is disposed between the first position sensor and the scanning and imaging device, and configured to measure a moving speed of the moving target in the passage, wherein upon receiving the sensing signal indicating that the moving target begins to enter the passage from the first position sensor, the control unit controls the speed sensor to measure the moving speed of the moving target, controls reconstruction of a scanned image based on the moving speed of the moving target received from the speed sensor, and corrects data of the scanned image based on the moving speed.

3. The apparatus according to claim 2, wherein the moving target passes through the passage at a speed in a predetermined speed range:
    if the moving target has a speed at an upper limit of the predetermined speed range, the scanning and imaging device performs sampling at a beam emitting frequency of the betatron; and
    if the moving target has a speed below the upper limit of the predetermined speed range, the scanning and imaging device is in an oversampling state, and the reconstruction of the scanned image is performed with either one of an interpolation method and a convolution method.

4. The apparatus according to claim 2, wherein the speed sensor comprises speed radar detectors disposed at the two sides of the passage.

5. The apparatus according to claim 3 wherein the control unit sends an instruction according to a sensing signal from the second position sensor, to switch an operating timing of a deflection coil of the betatron and thereby generate X-rays with different energy.

6. The apparatus according to claim 1, wherein either one of an overall vehicle scanning and a sectional scanning is performed on a car, a coach, a container truck, and a van, allowing passing thereof without requiring drivers to get off.

7. The apparatus according to claim 1, wherein the second position sensor is further configured to detect and recognize non-vehicles, cars, coaches, container trucks of trailer type, and vans.

8. The apparatus according to claim 1, wherein the control unit sends an instruction according to a sensing signal from the second position sensor, to switch an operating timing of a deflection coil of the betatron and thereby generate X-rays with different energy.

9. The apparatus according to claim 1, further comprising a third position sensor which is configured to determine whether the moving target has moved out of the passage, wherein the control unit sends a control signal to stop power supply to the betatron after the third position sensor detects that the moving target has entirely moved out of the radiation scanning area.

10. The apparatus according to claim 9, wherein the third position sensor comprises:
    a second ground induction coil buried underground and near an exit in the passage, and third rapid-response light curtain switches disposed at the two sides of the passage.

11. The apparatus according to claim 1, wherein the first position sensor comprises:
    a first ground induction coil buried underground at an entry to the passage, and first rapid-response light curtain switches disposed at two sides of the passage for use in conjunction with the first ground induction coil.

12. The apparatus according to claim 11, wherein pillars are installed at the two sides of the passage, and the rapid-response light curtain switches are disposed on the respective pillars.

13. The apparatus according to claim 1, wherein the second position sensor comprises second rapid-response light curtain switches disposed at the two sides of the passage, and photoelectric switches also disposed at the two sides of the passage.

14. A method for fast imaging and inspecting a moving target, comprising:
outputting from a first position sensor a sensing signal indicating whether a moving target begins to enter a passage for the moving target to pass therethrough;
detecting a type feature of the moving target, distinguishing a protected part of the moving target from an unprotected part of the same, sectioning the moving target, and outputting a sensing signal indicating whether the protected part of the moving target is passing or has already passed through a radiation scanning area, by use of a second position sensor;
powering on a betatron of a scanning and imaging device to place it in a standby state, upon receiving the sensing signal indicating that the moving target begins to enter the passage from the first position sensor, wherein the scanning and imaging device comprises the betatron for generating X-rays, and a detector for receiving X-rays penetrating through the moving target, and the betatron emits X-rays to the moving target passing through the passage to image the moving target; and
controlling a beam emitting time-point and a beam emitting mode of the betatron to correspondingly inspect respective sections of the moving target, when the second position sensor detects that the respective sections are passing through the radiation scanning area,
wherein a distance between the first position sensor and the scanning and imaging device is set to be greater than a predetermined value, such that a time period from a moment when the first position sensor detects the moving target to a moment when the moving target begins to enter the radiation scanning area is longer than or equal to a time period by which the betatron is powered on to reach the standby state.

15. The method according to claim 14, further comprising:
measuring a moving speed of the moving target in the passage by use of a speed sensor disposed between the first position sensor and the scanning and imaging device;
controlling the speed sensor to measure the moving speed of the moving target upon receiving the sensing signal indicating that the moving target begins to enter the passage from the first position sensor, and controlling reconstruction of the scanned image based on the moving speed of the moving target received from the speed sensor, and correcting data of the scanned image based on the moving speed.

16. The method according to claim 15, wherein the moving target passes through the passage at a speed in a predetermined speed range: if the moving target has a speed at an upper limit of the predetermined speed range, the scanning and imaging device performs sampling at a beam emitting frequency of the betatron; and
if the moving target has a speed below the upper limit of the predetermined speed range, the scanning and imaging device is in an oversampling state, and the reconstruction of the scanned image is performed with either one of an interpolation method and a convolution method.

17. The method according to claim 14, further comprising determining whether the moving target has moved out of the passage by use of a third position sensor, and sending a control signal to stop power supply to the betatron after the third position sensor detects that the moving target has entirely moved out of the radiation scanning area.

* * * * *